(12) United States Patent
Bassett et al.

(10) Patent No.: US 10,358,460 B2
(45) Date of Patent: Jul. 23, 2019

(54) PROTEIN MANUFACTURE

(71) Applicant: UCB BIOPHARMA SPRL, Brussels (BE)

(72) Inventors: Philip Bassett, Slough (GB); Richard Davies, Slough (GB); Elena Gonzalez, Slough (GB); Mark Pearce-Higgins, Slough (GB)

(73) Assignee: UCB BIOPHARMA SPRL, Brussels (BE)

( * ) Notice: Subject to any disclaimer, the term of this patent is extended or adjusted under 35 U.S.C. 154(b) by 0 days.

(21) Appl. No.: 15/538,269

(22) PCT Filed: Dec. 18, 2015

(86) PCT No.: PCT/EP2015/080561
§ 371 (c)(1),
(2) Date: Jun. 21, 2017

(87) PCT Pub. No.: WO2016/102383
PCT Pub. Date: Jun. 30, 2016

(65) Prior Publication Data
US 2017/0362272 A1    Dec. 21, 2017

(30) Foreign Application Priority Data

Dec. 22, 2014  (EP) .................................. 14199717

(51) Int. Cl.
| C07K 1/18 | (2006.01) |
|---|---|
| C07K 1/36 | (2006.01) |
| C07K 16/24 | (2006.01) |
| C07K 19/00 | (2006.01) |
| C07K 1/14 | (2006.01) |
| C12N 15/63 | (2006.01) |

(52) U.S. Cl.
CPC .............. *C07K 1/145* (2013.01); *C12N 15/63* (2013.01)

(58) Field of Classification Search
None
See application file for complete search history.

(56) References Cited

U.S. PATENT DOCUMENTS

| 8,426,168 B2 | 4/2013 | Stempfer et al. |
|---|---|---|
| 8,470,552 B2 | 6/2013 | Croughan et al. |
| 8,969,036 B2 | 3/2015 | Sehdev et al. |
| 2003/0219838 A1 | 11/2003 | Johnson |
| 2009/0252743 A1 | 10/2009 | Heavner et al. |
| 2013/0060009 A1 | 3/2013 | Bilgischer et al. |
| 2013/0178607 A1 | 7/2013 | Wild |

FOREIGN PATENT DOCUMENTS

| WO | WO 2005/019466 | 3/2005 | |
|---|---|---|---|
| WO | WO 2006/054063 | 5/2006 | |
| WO | WO-2011095506 A1 * | 8/2011 | ............ C07K 16/00 |
| WO | WO 2012/013930 | 2/2012 | |
| WO | WO 2016/102378 | 6/2016 | |

OTHER PUBLICATIONS

Graslund, S. et al. "Protein production and purification" *Nature Methods*, Feb. 1, 2008, pp. 135-146, vol. 5, No. 2.
Siegel, D. L. et al. "Expression and Characterization of Recombinant Anti-Rh(D) Antibodies on Filamentous Phage: A Model System for Isolating Human Red Blood Cell Antibodies by Repertoire Cloning" *Blood*, Apr. 15, 1994, pp. 2334-2344, vol. 83, No. 8.
Written Opinion in International Application No. PCT/EP2015/080561, dated Feb. 18, 2016, pp. 1-6.
Currently pending claims of U.S. Appl. No. 13/576,980, 2018, pp. 1-3.

* cited by examiner

*Primary Examiner* — Shulamith H Shafer
(74) *Attorney, Agent, or Firm* — Saliwanchik, Lloyd & Eisenschenk

(57) ABSTRACT

The present invention provides a novel method for protein manufacture wherein the protein is expressed in a host cell, and in a more specific manner relates to a method for manufacturing a protein that results in reduced levels of product-related impurities.

15 Claims, 4 Drawing Sheets

PROTEIN MANUFACTURE

CROSS-REFERENCE TO RELATED APPLICATION

This application is the U.S. national stage application of International Patent Application No. PCT/EP2015/080561, filed Dec. 18, 2015.

FIELD OF THE INVENTION

The present invention relates to a method for manufacturing a protein expressed in a host cell; in a more specific manner the invention relates to a method for manufacturing a protein that results in a protein with reduced levels of product-related impurities.

BACKGROUND OF THE INVENTION

In the field of therapeutics the use of proteins and antibodies and antibody-derived molecules in particular has been constantly gaining presence and importance, and, consequently, the need for controlled manufacturing processes has developed in parallel. The commercialization of therapeutic proteins, requires they are produced in large amounts. For this purpose the protein is frequently expressed in a host cell and subsequently be recovered and purified, prior to its preparation into an administrable form.

Depending on the protein to be expressed the choice of host cell may be a mammalian host cell, frequently a CHO (Chinese hamster ovary) cell, or a bacterial host cell. In the first case, the protein is typically secreted into the culture supernatant which is recovered, and the solution is then processed for protein purification.

When the host cell is a Gram negative prokaryotic cell, an often preferred expression system involves the newly synthesized protein accumulating within and being isolated from the periplasmic space. In this case, once the desired level of protein expression has been achieved, it is the cells that are harvested and processed. The protein is then recovered by means of subjecting the harvested cells to a protein extraction process which involves releasing the protein from the periplasm into solution and subsequent removal of cell debris and other impurities. These steps of cell harvest to protein release are typically included in what is termed primary recovery. The resulting protein-containing solution is then processed for protein purification. Preferred Gram negative prokaryotic cells used for periplasmic expression are generally *Escherichia coli* strains or *Pseudomonas fluorescens* cells.

Recovery of the heterologous protein expressed in the prokaryotic host cell during the primary extraction from the periplasmic space has often been a challenge. In this respect, different methods have been described in the prior art. For example, U.S. Pat. No. 8,969,036 describes the use of heat treatment to facilitate the subsequent isolation of functional Fab' fragments of antibodies. WO 2006/054063 describes the inclusion of a non-lysing treatment in combination with heat treatment at the primary extraction stage. WO 2005/019466 describes the inclusion of an interruption step after fermentation but prior to extraction. US 2013/0060009 describes the pH adjustment of samples prior to undergoing heat treatment during the extraction step.

However, another significant challenge is the high level of impurities present after primary extraction which increases the burden on subsequent purification steps and the overall efficiency of the entire purification process. These impurities may be in the form of cell debris, host cell proteins (HCP), DNA, or product related impurities such as truncated forms of the expressed product, aggregates or other modified forms such as deamidated, isomerized, oxidized or other conjugated forms. Of these, recombinant protein degradation products, also termed product-related impurities, are often the most difficult to remove during the heat extraction process and primary recovery given that they have very similar physico-chemical properties, such as melting temperature (Tm), to the target protein.

Although the resulting protein solution obtained after extraction will then be processed for protein purification, the level of purity of this solution impacts overall efficiency and costs associated to the purification steps, and therefore that of the total therapeutic protein production. This effect becomes even more apparent when considering large-scale protein manufacturing. In particular product-related impurities have an impact on the final product's quality profile, the control of which is particularly relevant for consistency across different batches.

As such there remains a need in the art for methods that improve impurity removal during protein extraction from cell culture.

DETAILED DESCRIPTION OF THE INVENTION

Figure 1:
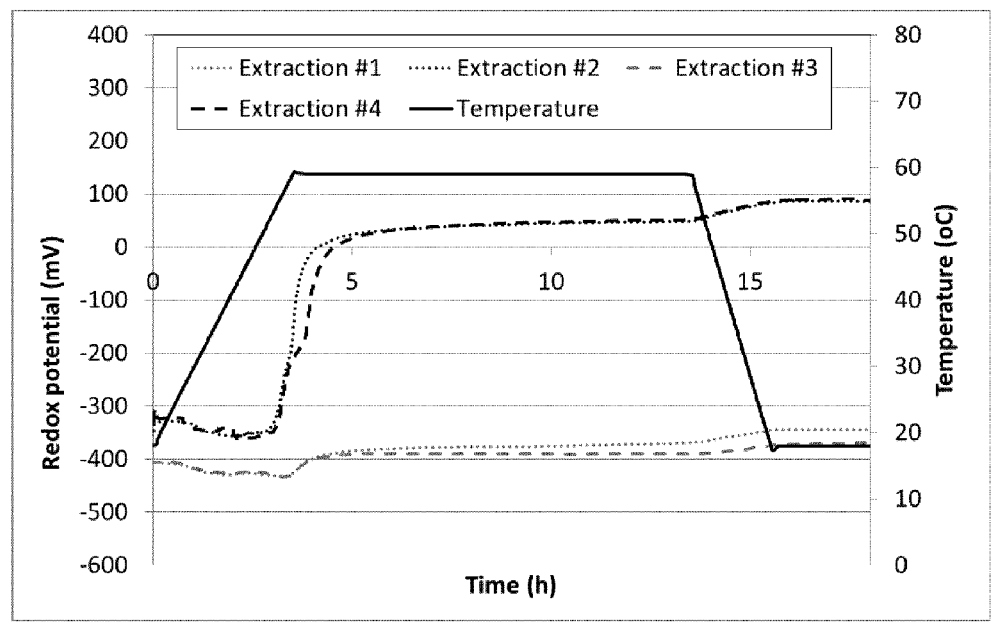
FIG. 1. Redox potential and temperature profiles of extractions. As may be observed, maintaining a nitrogen overlay during the heat treatment step maintains a low redox potential measurement throughout, with a minimum around −435 mV and typically −375 mV during temperature hold at 59° C. A similarly low redox potential was observed when the nitrogen was sparged. When the buffer containing host cells was overlaid with air in place of nitrogen, it can be seen that the redox potential values were significantly higher during the heat step extraction, becoming positive (typically around +45 mV) during the temperature hold at 59° C. A similarly high redox potential was observed when the air was sparged. The gaseous sparging was switched to overlay part way through the extractions due to the high levels of foaming observed.

The present invention resolves the above identified need by providing a novel method for protein manufacture wherein the protein is expressed in a host cell. In particular, the present invention provides a method suitable for industrial manufacture.

In a first embodiment the invention provides a method for manufacturing a protein of interest wherein said protein is expressed in a host cell, comprising
culturing said host cells under conditions such that they express said protein,
collecting the host cells from the cell culture fluid,
adding buffer to the host cells, and
subjecting the host cells in buffer to heat treatment wherein the redox potential of the buffer is maintained below 0 mV during said heat treatment.

In a particular embodiment, host cells are prokaryotic cells, such as gram-negative bacteria. In another embodiment, the host cells are E. coli cells or P. fluorescens cells. Prokaryotic host cells for protein expression are well known in the art (Terpe, K. (2006). Overview of bacterial expression systems for heterologous protein production: from molecular and biochemical fundamentals to commercial systems. Appl Microbiol Biotechnol 72, 211-222.). Host cells according to the invention include recombinant cells which have been genetically engineered to produce the protein of interest such as an antibody fragment. The recombinant E. coli host cells may be derived from any suitable E. coli strain including from MC4100, TG1, TG2, DHB4, DH5α, DH1, BL21, K12, XL1Blue and JM109. One example is E. coli strain W3110 (ATCC 27,325) a commonly used host strain for recombinant protein fermentations. Antibody fragments can also be produced by culturing modified E. coli strains, for example metabolic mutants or protease deficient E. coli strains, such as disclosed in WO 2011/086138, WO 2011/086139, WO 2011/086136 and WO 2013/007388 which are incorporated herein in its entirety.

A protein of interest that can be purified in accordance with the methods of the present invention is typically isolated from the periplasm of the E. coli host cell. The methods for targeting proteins to this compartment are well known in the art (Makrides, S. C. (1996). Strategies for achieving high-level expression of genes in Escherichia coli. Microbiol Rev 60, 512-538.). Examples of suitable signal sequences to direct proteins to the periplasm of E. coli include the E. coli PhoA, OmpA, OmpT, LamB and OmpF signal sequences.

Expression of the recombinant protein in the E. coli host cells may also be under the control of an inducible system, whereby the expression of the recombinant antibody in E. coli is under the control of an inducible promoter. Many inducible promoters suitable for use in E. coli are well known in the art and depending on the promoter expression of the recombinant protein can be induced by varying factors such as temperature or the concentration of a particular substance in the growth medium. Examples of inducible promoters include the E. coli lac, tac, and trc promoters which are inducible with lactose or the non-hydrolyzable lactose analog, isopropyl-b-D-1-thiogalactopyranoside (IPTG) and the phoA, trp and araBAD promoters which are induced by phosphate, tryptophan and L-arabinose respectively. Expression may be induced by, for example, the addition of an inducer or a change in temperature where induction is temperature dependent. Where induction of recombinant protein expression is achieved by the addition of an inducer to the culture the inducer may be added by any suitable method depending on the fermentation system and the inducer, for example, by single or multiple shot additions or by a gradual addition of inducer through a feed. It will be appreciated that there may be a delay between the addition of the inducer and the actual induction of protein expression for example where the inducer is lactose there may be a delay before induction of protein expression occurs while any pre-existing carbon source is utilized before lactose.

Alternatively, the protein of interest that can be purified in accordance with the methods of the present invention is isolated from the periplasm of P. fluorescens. Suitable sequences that direct proteins to the periplasmic compartment in P. fluorescens include sec-type secretion leaders as have been described in the art (D. M. Retallack, et al. Transport of heterologous proteins to the periplasmic space of Pseudomonas fluorescens using a variety of native signal sequences Biotechnol. Lett., 29 (2007), pp. 1483-1491). Expression of the protein of interest may be under the control of an inducible system, whereby expression is under control of an inducible promoter as described in preceding paragraph. Well known inducers such as IPTG may be used in this context, alternatively inducers such as benzoate of anthranilate that induce Pben509 and Pben278 promoters, respectively have been described in P. fluorescens expression systems.

Prokaryotic host cell cultures (fermentations) may be cultured in any medium that will support the growth of the host cells and expression of the recombinant protein. The medium may be any chemically defined medium, such as e.g. described for *E. coli* in Durany O, et al. (2004). Studies on the expression of recombinant fuculose-1-phosphate aldolase in *Escherichia coli*. Process Biochem 39, 1677-1684.

Fermentation of prokaryotic host cells may be performed in any suitable system, for example continuous, batch or fed-batch mode depending on the protein and the yields required. Batch mode may be used with shot additions of nutrients or inducers where required. Alternatively, a fed-batch culture may be used and the cultures grown in batch mode pre-induction at the maximum specific growth rate that can be sustained using the nutrients initially present in the fermenter and one or more nutrient feed regimes used to control the growth rate until fermentation is complete. Fed-batch mode may also be used pre-induction to control the metabolism of the prokaryotic host cells and to allow higher cell densities to be reached.

The host cells are then collected from the fermentation medium, e.g. host cells are collected from the sample by centrifugation, filtration or by concentration.

In one embodiment of the method according to the present invention the step of cell collection comprises a step of centrifugation and cell recovery. In a particular preferred embodiment of the invention, said step of centrifugation is continuous centrifugation, from which a cell slurry is recovered.

For prokaryotic (e.g. *E. coli*) host cell culture processes wherein the protein of interest such as an antibody fragment is found in the periplasmic space of the host cell it is required to release the protein from the host cell. The release may be achieved by any suitable method or combination of methods such as cell lysis by mechanical or pressure treatment, freeze-thaw treatment, osmotic shock, extraction agents and/or heat treatment. Such extraction methods for protein release are well known in the art. In the method of the present invention, protein extraction is achieved by a heat treatment step, i.e. maintaining the sample at an elevated temperature during a defined period.

According to the method of the present invention buffer is added to the cells collected from the cell culture fluid prior to the heat treatment step. In a particular embodiment of the method of the invention, said buffer is 100 mM Tris and 10 mM EDTA at pH 7.4, in a further embodiment said extraction buffer is 75 mM Tris and 7.5 mM EDTA at pH 7.4, 200 mM Tris and 20 mM EDTA at pH 7.4, or 300 mM Tris and 30 mM EDTA at pH 7.4. In one embodiment of the invention the buffer has a pH which ensures that the pH of the sample is pH 6 to 9, for example pH 6 to 8, prior to the heat treatment step as described in WO 2012/013930 which is incorporated herein in its entirety. Preferably said pH is 6.5 to 8, pH 6.8 to 7.8, or pH 7 to 7.6.

The skilled artisan would know of further suitable buffers described in the art to be used for protein extraction.

In a further alternative embodiment the redox potential of said buffer is maintained below −100 mV, −200 mV, below −300 mV or below −400 mV.

The redox potential of the environment is particularly critical for the dynamics of the disulfide bonds between thiol groups on cysteine residues present in protein molecules. When reduced, said disulfide bonds are disrupted freeing the corresponding thiol groups (—SH). Antibody molecules have several disulfide bonds, which are critical to maintaining their structure, and hence their biological activity. Some of these disulfide bonds are more accessible than others to reducing and/or oxidizing species present in the environment given their position within the molecule, and consequently more susceptible to disruption.

In the context of the present invention, product-related impurities are in fact fragments of the protein of interest and therefore smaller and simpler in structure. Without wishing to be bound by theory the cysteine bonds within said product-related impurities are more accessible and therefore more susceptible to disruption as a consequence of the redox potential of the environment.

In a second embodiment of the method of the invention said heat treatment is performed in a container and said redox potential is maintained by reducing the amount of oxygen ($O_2$) present in the gaseous phase in the container during the heat treatment.

Generally there is a volume of air in the container (referred to herein as the gaseous phase) above the sample composed of buffer and host cells. Within the meaning of the present invention, reducing the amount of oxygen in the gaseous phase, means altering the composition of said gaseous phase in a manner such that it contains less oxygen than air. As is known in the art, air typically contains approximately 21% oxygen (volume).

In order to maintain the redox potential below 0 mV according to the method of the invention, a skilled artisan would be aware of different means available to prevent oxidation of the extraction sample. This may be achieved by removal of oxygen and other oxidizing gases present in the gaseous phase in the container, typically by displacement with another inert gas. Said displacement may be achieved by means of a nitrogen ($N_2$) overlay, i.e. maintaining the sample in the container in contact a $N_2$ containing gaseous phase, or by sparging, i.e. bubbling or passing, the inert gas through the sample into the container. Other inert gases that may be used to maintain a redox potential according to the method of the invention include argon and helium.

Alternatively, there is a choice of reducing agents available in the art, that have varying degrees of strength. Consequently a skilled artisan would choose the most appropriate reducing agent depending on the desired redox potential and the time during which it should be maintained. Known reducing agents in the art include but are not limited to glutathione, mercaptoethanol, dithiothreitol or Tris(2-carboxyethyl)phosphine.

Culturing of prokaryotic host cells can take place in any suitable container such as a shake flask or a fermenter depending on the scale of production required. Various large scale fermenters are available with a capacity of more than 1,000 liters up to about 100,000 liters. Preferably, fermenters of 1,000 to 50,000 liters are used, more preferably 1,000 to 25,000 or 1,000 to 20,000, 1,000 to 15,000, 1,000 to 10,000, 1,000 to 5,000, 20,000, 15,000, 12,000 10,000, 5000 or 2000 liters. Smaller scale fermenters may also be used with a capacity of between 0.5 and 1,000 liters.

In a preferred embodiment, said gaseous phase contains less than 20%, 15%, 12%, 10%, 8%, 5%, 2% or 1% oxygen (volume) during the heat treatment step.

In a preferred embodiment, said oxygen is essentially excluded from the gaseous phase during the heat treatment step.

In a third embodiment of the method of the invention, nitrogen ($N_2$) is added to the gaseous phase of the container.

In a fourth embodiment of the method of the invention said gaseous phase contains at least 80% $N_2$, at least 85%, at least 90% $N_2$, at least 95% $N_2$ or at least 97% or 99% $N_2$. In a further alternative embodiment, said gaseous phase is essentially $N_2$.

Typically, said $N_2$ is added to the gaseous phase of the container as an overlay and is maintained in the headspace of the container containing the buffer and the host cells by adding 100% $N_2$ gas to the headspace with from 0.1 to 1 vvm (volume of gas per volume of liquid per minute, i.e. 1 L/min for a 1 L extraction volume).

In a particular embodiment the present invention refers to a method for manufacturing a protein of interest wherein said protein is expressed in a host cell, comprising culturing said host cells under conditions such that they express said protein,
collecting the host cells from the cell culture fluid,
adding buffer to the host cells, and
subjecting the host cells in buffer to heat treatment in a container wherein the gaseous phase of the container is essentially $N_2$.

Depending on the configuration of the container, said $N_2$ may be added to the gaseous phase of the container, wherein the container is subsequently sealed, i.e. isolating the interior of the container from the outside, leaving the $N_2$ in the gaseous phase during the heat treatment. Alternatively, a constant flow of $N_2$ is applied through the gaseous phase of the container during the heat treatment step, e.g. for containers that do not allow the possibility of sealing the interior from the outside environment.

In one embodiment the $N_2$ is added to or introduced in the gaseous phase before the heat treatment step to ensure the redox potential is maintained below the desired value during the heat treatment step.

In a particular embodiment, the method of the invention comprises:

culturing said host cells under conditions such that they express the protein of interest,
collecting the host cells from the cell culture fluid,
adding buffer to the host cells in a container,
adding $N_2$ to the gaseous phase of the container,
sealing said container; and
subjecting the host cells in buffer to heat treatment in the container wherein the redox potential of said buffer is maintained below 0 mV during said heat treatment.

Therefore in a further embodiment of the method of the invention, said $N_2$ is introduced as an overlay using at least 80%, at least 85%, at least 90%, at least 95%, at least 97%, at least 99% or 100% $N_2$.

In an alternative embodiment of the invention, said $N_2$ is introduced by sparging $N_2$ through the buffer during the heat treatment, preferably by sparging essentially pure $N_2$.

In a fifth embodiment of the invention, said $N_2$ is added to the container as an overlay in the gaseous phase of the container or by sparging the $N_2$ through the buffer.

The method according to the invention comprises a heat treatment step that makes it possible to obtain a sample of soluble, correctly folded and assembled protein such as an antibody fragment by facilitating the removal of other protein-related material.

Protein which is "correctly folded and assembled" is shown by the presence of a single band corresponding to the expected molecular weight for the assembled protein chain on non-reducing SDS-PAGE. Other protein related material will typically be partially degraded fragments of correctly folded and assembled protein.

The heat treatment step in the method of the present invention is a step of maintaining the temperature of the sample at a desired elevated temperature once this desired elevated temperature has been reached during a heat up phase.

The heat treatment step is performed by subjecting the sample to a desired elevated temperature. Most preferably, heat treatment step is performed within the range of 30° C. to 70° C. The temperature can be selected as desired and may depend on the stability of the protein for purification. In another embodiment, the temperature is within the range 40° C. to 65° C., or preferably within the range 40° C. to 60° C., more preferably within the range 45° C. to 60° C., even more preferably within the range 50° C. to 60° C. and most preferably at 55° C. to 60° C., 58° C. to 60° C. or 59° C. Thus, the minimum temperatures are 30° C., 35° C. or 40° C. and the maximum temperatures 60° C., 65° C. or 70° C.

In a sixth embodiment of the method of the invention, said heat treatment step is performed at 30° C. to 70° C.

In a seventh embodiment of the method of the invention, said heat treatment step is performed at 55° C. to 65° C.

The heat treatment step is preferably carried out for a prolonged period of time. The length of heat treatment is preferably between 1 and 24 hours, or between 1 and 18 hours, more preferably between 4 and 18 hours, even more preferably between 6 and 16 hours, and most preferably between 8 and 14 hours or between 8 and 12 hours, for example 10 hours. Thus, the minimum time for heat treatment is 1, 2 or 3 hours and the maximum is 20, 22 or 24 hours.

In an eighth embodiment of the method of the invention, the heat treatment step of the sixth or seventh embodiment is maintained for 1 hour to 18 hours.

As a skilled artisan knows, there generally exists an inversely proportional relationship between reaction times and temperatures, whereby the higher the temperature at which a reaction is performed the shorter the time necessary for the reaction to take place.

In a particular embodiment, the heat treatment is performed at 50° C. to 60° C. for 10 to 16 hours, and more preferably at 59° C. for 10 to 12 hours. One skilled in the art will understand that temperatures and time can be selected as suits the sample in question and the characteristics of the protein of interest such as an antibody or antibody fragment.

In a further alternative embodiment of the method of the invention, said protein extraction is performed at a temperature from 58° C. to 60° C. for a period of 8 to 12 hours.

The heat treatment step is preferably carried out with agitation of the sample such as in a shaker or stirrer set to operate at a suitable agitation rate, such as 200 rounds per minute (RPM). However, the suitable agitation rate will vary depending upon the scale of the method.

In a ninth embodiment of the method of the invention, the sample has or is adjusted to a pH of 6 to 9 before the heat treatment step. In a further particular embodiment of the method of the invention, the pH of said sample is 6.5 to 8, 6.5 to 7.5, or 6.8 to 7.2 before the heat treatment step.

In a particular embodiment, the pH of the sample is measured or adjusted before the heat treatment step, to ensure that the pH of the sample during the heat treatment step is 5 to 9, preferably the pH of the sample during the heat treatment step is 6 to 7.

In a further embodiment the pH is adjusted with a base such as an inorganic base for example sodium hydroxide or an organic base such as triethylamine or trimethylamine or tris base.

Any suitable agent may be used to adjust the pH of the sample. The agent may be the buffer or may be added before and/or after the buffer. Typical agents which may be used to adjust the pH comprise or consist of one or more of the following: NaOH, NH$_4$OH, sulphuric acid, EDTA, Tris buffer.

In a further particular embodiment, the pH of the sample is measured or adjusted before the heat treatment step and before addition of an inert gas such as nitrogen to the gaseous phase of the container in order to maintain the redox potential below 0 mV. Alternatively, in another embodiment of the invention, the pH of the sample is measured and/or adjusted before the heat treatment step and the inert gas such as nitrogen is passed through the sample during the heat treatment step.

The pH measurements referred to herein are generally normalized to 20° C.

In the context of the present invention "before the heat treatment step" means prior to and including the point in time at which the sample reaches the desired elevated temperature and the heat treatment step (holding at an elevated temperature) commences. In order to reach the desired elevated temperature for the heat treatment step the sample is subjected to a "heat up phase" during which the temperature of the sample is elevated to the desired temperature. In one embodiment, the method according to the invention comprises subjecting the sample to a heat up phase and a heat treatment step. In the embodiment wherein the method comprises subjecting the sample to a heat up phase and a heat treatment step, the sample may be at the required pH level prior to the start of the heat up phase and/or at the required pH level during the heat up phase.

In a particular embodiment, N$_2$ is added to the gaseous phase of the container prior to the start of the heat up phase. Preferably the sample is at the required pH level prior to said heat up phase.

In a tenth embodiment of the method of the invention, the protein of interest is a recombinant protein encoded in an expression vector.

In an eleventh embodiment, the method according to the eighth embodiment of the invention, the protein is a recombinant antibody.

In a twelfth embodiment said recombinant antibody is a recombinant antibody fragment. There are many recombinant antibody fragments known in the art including Fab, Fab', F(ab')$_2$, and Fv and scFv fragments. Alternatively the recombinant antibody is selected from diabodies, triabodies, tetrabodies, minibodies, domain antibodies, single-chain antibodies, bispecific, trispecific, tetraspecific or multispecific antibodies formed from antibody fragments or antibodies, including but not limited to Fab-Fv constructs.

In a thirteenth embodiment of the method of the invention, said recombinant antibody or recombinant antibody fragment specifically binds to TNF-alpha or to CD154.

In one embodiment, the present invention provides a method for the manufacture of a recombinant antibody wherein said recombinant antibody is expressed in a host cell, comprising culturing said host cells under conditions such that they express said protein, collecting the host cells from the cell culture fluid, adding buffer to the host cells, and subjecting the host cells to heat treatment to extract the recombinant antibody from said host cells in a container wherein the redox potential of said buffer is maintained below 0 mV, below –100 mV, below –200 mV, below –300 mV or below –400 mV, during said extraction.

In another particular embodiment, the present invention provides a method for the manufacture of a recombinant antibody wherein said recombinant antibody is expressed in a host cell, comprising culturing said host cells under conditions such that they express said protein, collecting the host cells from the cell culture fluid, adding buffer to the host cells in a container, adding N$_2$ to the gaseous phase of the container, subjecting the host cells to heat treatment, and recovering said protein.

In another particular embodiment the method of the invention, provides a method for the manufacture of a recombinant antibody wherein said recombinant antibody is expressed in a host cell, comprising culturing said host cells under conditions such that they express said protein, collecting the host cells from the cell culture fluid, adding buffer to the host cells in a container, adding N$_2$ to the gaseous phase of the container, subjecting the host cells to heat treatment, and recovering said protein; wherein said recovered protein has a lower level of product-related impurities as compared to protein recovered from a method of manufacture comprising a heat treatment performed without the presence of N$_2$ in the gaseous phase of the container.

The method according to the present invention may comprise one or more further steps, such as purification procedures such as filtration and/or centrifugation. Also included is fluidized bed chromatography. Preferred further purification procedures include ion exchange chromatography, microfiltration, ultrafiltration, diafiltration, and fixed bed capture and expanded bed capture and combinations of any of these.

The term "antibody" or "antibodies" as used herein refers to monoclonal or polyclonal antibodies. The term "antibody" or "antibodies" as used herein includes but is not limited to recombinant antibodies that are generated by recombinant technologies as known in the art. "Antibody" or "antibodies" include antibodies' of any species, in particular of mammalian species; such as human antibodies of any isotype, including IgA$_1$, IgA$_2$, IgD, IgG$_1$, IgG$_{2a}$, IgG$_{2b}$, IgG$_3$, IgG$_4$ IgE and IgM and modified variants thereof, non-human primate antibodies, e.g. from chimpanzee, baboon, rhesus or cynomolgus monkey; rodent antibodies, e.g. from mouse, rat or rabbit; goat or horse antibodies; and camelid antibodies (e.g. from camels or llamas such as Nanobodies™) and derivatives thereof; or of bird species such as chicken antibodies or of fish species such as shark antibodies. The term "antibody" or "antibodies" also refers to "chimeric" antibodies in which a first portion of at least one heavy and/or light chain antibody sequence is from a first species and a second portion of the heavy and/or light chain antibody sequence is from a second species. Chimeric antibodies of interest herein include "primatized" antibodies comprising variable domain antigen-binding sequences derived from a non-human primate (e.g. Old World Monkey, such as baboon, rhesus or cynomolgus monkey) and human constant region sequences. "Humanized" antibodies are chimeric antibodies that contain a sequence derived from non-human antibodies. For the most part, humanized antibodies are human antibodies (recipient antibody) in which residues from a hypervariable region of the recipient are replaced by residues from a hypervariable region [or complementarity determining region (CDR)] of a non-human species (donor antibody) such as mouse, rat, rabbit, chicken or non-human primate, having the desired specificity, affinity, and activity. In most instances residues of the human (recipient) antibody outside of the CDR; i.e. in the framework region (FR), are additionally replaced by corresponding non-human residues. Furthermore, humanized antibodies may comprise residues that are not found in the recipient antibody or in the donor antibody. These modifications are made to further refine antibody performance. Humanization reduces the immunogenicity of non-human antibodies in humans, thus facilitating the application of antibodies to the treatment of human disease. Humanized antibodies and several different technologies to generate them are well known in the art. The term "antibody" or "antibodies" also refers to human antibodies, which can be generated as an alternative to humanization. For example, it is possible to produce transgenic animals (e.g., mice) that are capable, upon immunization, of producing a full repertoire of human antibodies in the absence of production of endogenous murine antibodies. For example, it has been described that the homozygous deletion of the antibody heavy-chain joining region (JH) gene in chimeric and germ-line mutant mice results in complete inhibition of endogenous antibody production. Transfer of the human germ-line immunoglobulin gene array in such germ-line mutant mice will result in the production of human antibodies with specificity against a particular antigen upon immunization of the transgenic animal carrying the human germ-line immunoglobulin genes with said antigen. Technologies for producing such transgenic animals and technologies for isolating and producing the human antibodies from such transgenic animals are known in the art. Alternatively, in the transgenic animal; e.g. mouse, only the immunoglobulin genes coding for the variable regions of the mouse antibody are replaced with corresponding human variable immunoglobulin gene sequences. The mouse germline immunoglobulin genes coding for the antibody constant regions remain unchanged. In this way, the antibody effector functions in the immune system of the transgenic mouse and consequently the B cell development is essentially unchanged, which may lead to an improved antibody response upon antigenic challenge in vivo. Once the genes coding for a particular antibody of interest have been isolated from such transgenic animals the genes coding for the constant regions can be replaced with human constant region genes in order to obtain a fully human antibody. Other methods for obtaining human antibodies/antibody fragments in vitro are based on display technologies such as phage display or ribosome display technology, wherein recombinant DNA libraries are used that are either generated at least in part artificially or from immunoglobulin variable (V) domain gene repertoires of donors. Phage and ribosome display technologies for generating human antibodies are well known in the art. Human antibodies may also be generated from isolated human B cells that are ex vivo immunized with an antigen of interest and subsequently fused to generate hybridomas which can then be screened for the optimal human antibody. The term "antibody" or "antibodies" as used herein, also refers to an aglycosylated antibody.

In certain embodiments of this invention, the antibodies are antibodies that are modified by covalent attachment of functional moieties such as water-soluble polymers, such as poly(ethyleneglycol), copolymers of poly(ethyleneglycol) and poly(propyleneglycol), carboxymethyl cellulose, dextran, poly(vinylalcohol), poly(vinylpyrrolidone) or poly (proline)—all of which are known to exhibit substantially longer half-lives in blood following intravenous injection than do the corresponding unmodified proteins.

In some embodiments, antibodies of the present invention are antibodies attached to functional moieties such as to poly(ethyleneglycol) (PEG) moieties. In one particular embodiment, the antibody is an antibody fragment and the PEG molecules may be attached through any available amino acid side-chain or terminal amino acid functional group located in the antibody fragment, for example any free amino, imino, thiol, hydroxyl or carboxyl group. Such amino acids may occur naturally in the antibody fragment or may be engineered into the fragment using recombinant DNA methods (see for example U.S. Pat. No. 5,219,996; 5,667,425; WO 98/25971).

The term "antibody" or "antibodies" as used herein not only refers to untruncated antibodies of any species, including from human (e.g. IgG) and other mammalian species, but also refers to an antibody fragment. A fragment of an antibody comprises at least one heavy or light chain immunoglobulin domain as known in the art and binds to one or more antigen(s). Examples of antibody fragments according to the invention include Fab, Fab', F(ab')2, and Fv and scFv fragments; as well as diabodies, triabodies, tetrabodies, minibodies, domain antibodies (dAbs), such as sdAbs, $V_HH$ and $V_{NAR}$ fragments, single-chain antibodies, bispecific, trispecific, tetraspecific or multispecific antibodies formed from antibody fragments or antibodies, including but not limited to Fab-Fv or Fab-Fv-Fv constructs. Antibody fragments as defined above are known in the art.

The term "redox potential" as used herein refers to the measure of the tendency of a chemical species to acquire electrons and thereby be reduced. Redox potential is measured in volts (V), or millivolts (mV). Each species has its own intrinsic reduction potential; the more positive the potential, the greater the species' affinity for electrons and tendency to be reduced.

The term "extraction" or "protein extraction" as used herein refers to removing the protein expressed within a host cell from the host cell. Extraction can involve the disruption of the host cell and the isolation of intracellular fluid from cell debris, or the manipulation of the host to make the outer cell membrane of gram-negative bacteria or other cells having an outer cell membrane leaky in order to release the fluid of the periplasmic space from such cells.

EXAMPLES

Methods
Fermentation Process A

E. coli W3110 transfected with a vector so as to express a Fab' binding specifically to human TNF-alpha were used as host cells.

A frozen cell bank vial containing these cells was used to inoculate a shake flask (700 ml total volume) containing 6× peptone-yeast extract (6×P-Y) medium plus tetracycline. This shake flask was incubated at 30° C. and 230 rpm. At the required OD range (OD600=2-3), the shake flask was used to inoculate a seed fermenter (10 L total volume) containing SM6 chemically defined media (Popplewell et al. Expression of Antibody Fragments by Periplasmic Secretion in *Escherichia coli*; Methods in Molecular Biology, vol. 308: Therapeutic Proteins: Methods and Protocols; 2005) plus tetracycline, with glycerol as the carbon source. The cell culture within the seed fermenter was maintained at 30° C., dissolved oxygen concentration ($pO_2$) was maintained at 30% and pH was controlled at 7.0.

At the required OD range (OD600=30-37), the seed culture was used to inoculate the production fermenter (600 L total volume) containing chemically defined media with glycerol as the carbon source. The production fermenter was initially maintained at 30° C., 30% $pO_2$, and pH was controlled at 7.0, and cells grown in batch phase until induction. During the batch phase the temperature was reduced to 25° C. and an addition of $MgSO_4$ was made to avoid depletion of this metabolite.

At a specific OD range (OD600=43-47), during which glycerol depletion occurs, a bolus addition of lactose solution was made to the culture. Lactose would be then utilized by the cells as the main carbon source and would also act as an inducer of the Fab' expression. The concentration of lactose was maintained through the induction phase via a continuous feed and cells were harvested 30 hours post induction.

Fermentation Process B

A frozen cell bank vial containing E. coli MXE012 host cells Fab' expressing a Fab' binding specifically to human TNF-alpha was used to inoculate a shake flask (700 ml total volume) containing 6× peptone-yeast extract (6×P-Y) medium plus tetracycline. This shake flask was incubated at 30° C. and 230 rpm. At the required OD range (OD600=2-3), the shake flask was used to inoculate a seed fermenter (10 L total volume) containing MD chemically defined media (Durany et al. 2004. Studies on the expression of recombinant fuculose-1-phosphate aldolase in Escherichia coli. Process Biochem 39:1677-1684 plus tetracycline, with glycerol as the carbon source. The cell culture within the seed fermenter was maintained at 30° C., dissolved oxygen concentration ($pO_2$) was maintained at 30% and pH was controlled at 6.9.

At the required OD range (OD600=30-37), the seed culture was used to inoculate the production fermenter (600 L total volume) containing chemically defined media with glycerol as the carbon source. The production fermenter was initially maintained at 30° C., 30% $pO_2$, with pH controlled at pH 6.9 and grown in batch phase until the glycerol was depleted. During this time an addition of $MgSO_4$ was made to avoid depletion of this metabolite.

At the end of the batch phase, an exponential glycerol feed was switched on and the culture was fed a specific amount of glycerol to achieve an OD600 of approximately 70 units. At this point, the glycerol feed was switched from an exponential feed to a linear feed and Fab' expression was induced by the addition of IPTG (38.79 g/kg of culture). Cells were harvested 40 hours post induction.

E. coli strain MXE012 is a metabolic E. coli mutant containing the mutation sprH145A to the spr gene as described in WO 2011/086136 (incorporated herein in its entirety).

Recovery and Extraction Methods

Cells were harvested by continuous centrifugation using a Westfalia PSC 5 disk stack centrifuge.

Concentrated cell slurry was resuspended back to the original cell harvest concentration in 2 L or 5 L glass vessels by the addition of water and extraction buffer at pH 7.4 to a final extraction buffer concentration of 10 mM EDTA, 100 mM Tris.

Where required, resuspended cells were adjusted to pH 7.2 by the addition of 2.5 M Tris base to the extraction buffer before protein extraction via a heat step. For heat extraction, the cells were heated to 59° C. for 10 hours. Temperature and mixing were maintained using Biostat BPlus control units (Sartorius) and Multiple Fermenter Control System (MFCS®) software.

Sample Purification

Fab'-related species were purified from extraction samples to enable the assessment of product-related impurities. Extraction samples were first clarified by centrifugation, collection of the clarified supernatant and filtration through a 0.2 μm filter. Clarified supernatant was then loaded onto 1 mL Protein L columns (Pierce #89928), washed with a low concentration phosphate buffer at pH 7.4 and eluted with a glycine buffer at pH 2.8. It was demonstrated that the Protein L resin could capture Fab' fragments and that the recovery was linear and reproducible within the experimental range.

Sample Analysis

Purified samples were analysed and quantified by Cation Exchange chromatography. Samples were loaded onto a Dionex Pro Pac SCX-10 (Thermo Scientific) analytical column and eluted using a salt gradient. Eluted proteins were monitored at 280 nm and chromatogram peaks were quantified and interpreted according to a standard procedure.

Example 1

Fermentation was carried out according to process B and protein was extracted as described above. Redox potential was measured during the extraction process in the containers using ORP (Oxidation-Reduction Potential) probes (Broadley James Corporation, Irvine Calif.) and monitored using MFCS® software (Sartorius, Bethlehem Pa.).

In order to assess the effect of maintaining a reduced redox environment, some extraction containers were exposed to nitrogen and others were exposed to air during extraction, also the gas was either sparged through the sample into the containers or maintained as an overlay flow to the headspace of the containers.

Table 1 below shows a summary of container gas-flow conditions. All gas flows were maintained at a flow-rate of 1 vvm (volume of gas per volume of liquid per minute, i.e. 1 L/min for a 1 L extraction) using 100% nitrogen or compressed air supply.

TABLE 1

| Extraction # | Condition |
|---|---|
| 1 | $N_2$ Overlay |
| 2 | Air Overlay |
| 3 | $N_2$ Sparged |
| 4 | Air Sparged |

Figure 2:
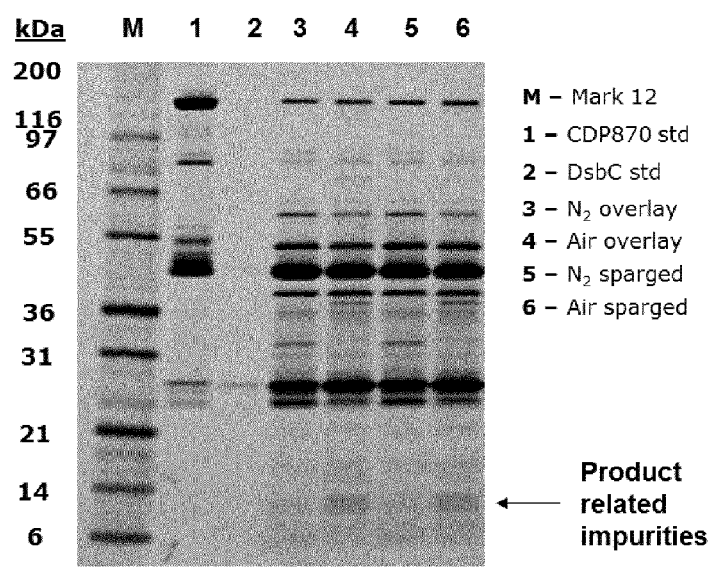
FIG. 2. SDS-PAGE gel of post-extraction samples. Lane M depicts molecular weight standard markers (Mark 12, Invitrogen). Lane 1 is an anti-TNF alpha Fab' reference standard. Lane 2 is a DsbC standard (disulphide bond isomerase protein). Lane 3 is a sample post extraction where a nitrogen overlay was applied during extraction. Lane 4 is a sample post extraction where an air overlay was applied during extraction. Lane 5 is a sample post extraction where nitrogen was sparged through the sample during extraction. Lane 6 is a sample post extraction where air was sparged through the sample during extraction. The figure shows that in the presence of nitrogen, the reducing conditions during heat extraction are sufficient to enable significant reduction in the level of product-related impurities as compared to extractions performed in the presence of air.

FIGS. 1 and 2 show the corresponding redox and temperature profiles of the extractions (FIG. 1) and an SDS PAGE gel of post-extraction samples (FIG. 2).

As can be derived from these figures, maintaining a nitrogen overlay during the heat treatment step maintains a low redox potential measurement throughout, with a minimum around −435 mV and typically −375 mV during temperature hold at 59° C. A similarly low redox potential was observed when the nitrogen was sparged. When the buffer containing host cells was overlaid with air in place of nitrogen, it can be seen that the redox potential values were significantly higher during the heat step extraction, becoming positive (typically around +45 mV) during the temperature hold at 59° C. A similarly high redox potential was observed when the air was sparged. The gaseous sparging was switched to overlay part way through the extractions due to the high levels of foaming observed.

FIG. 2 demonstrates a significant difference in the level of product-related impurity as measured by SDS PAGE. The figure shows that in the presence of nitrogen, the reducing conditions during heat extraction are sufficient to enable significant reduction in the level of product-related impurities as compared to extractions performed in the presence of air.

Example 2

Fermentation according to process A and subsequent extraction were performed as described above. Nitrogen flow-rate to the headspace was varied from 0.1 vvm to 1 vvm in combination with varied stirring and fill volumes according to Table 2.

TABLE 2

| Extraction Number | Nitrogen Overlay (vvm) | rpm | Fill volume |
|---|---|---|---|
| 1 | 0.1 | 150 | 1.5 |
| 2 | 1 | 150 | 1.5 |
| 3 | 0.1 | 450 | 3 |
| 4 | 1 | 450 | 3 |
| 5 | 0.55 | 300 | 2.25 |
| 6 | 0.55 | 300 | 2.25 |
| 7 | 0.55 | 300 | 2.25 |
| 8 | 0 | 300 | 2.25 |

Figure 3:
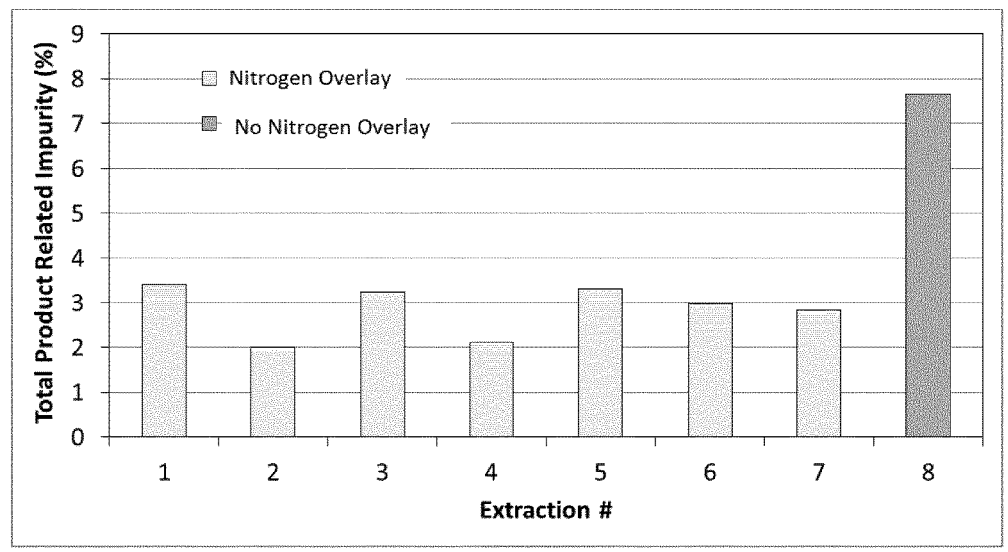
FIG. 3. Total Fab' fragments expressed as % of all product related species as measured by CEX HPLC following Protein L purification. A clear effect of having a nitrogen overlay on the clearance of product-related impurities may be observed. Extraction #8, where no nitrogen overlay was applied, had significantly higher levels of product-related impurities. On the other hand, the figure also suggests that the rate of nitrogen overlay might have an effect on the clearance of this impurity, comparing extractions 1 to 2, and 7 to 8.

As may be seen in FIG. 3, a clear effect of having a nitrogen overlay on the clearance of product-related impurities may be observed. Extraction #8, where no nitrogen overlay was applied, had significantly higher levels of product-related impurities. On the other hand, the figure also suggests that the rate of nitrogen overlay might have an effect on the clearance of this impurity, comparing extractions 1 to 2, and 7 to 8.

Example 3

Fermentation according to process A and cell harvest were carried out as described above. Resuspended host cells were adjusted to pH 7.2 by the addition of 2.5 M Tris base to the extraction buffer. immediately prior to heat extraction. This heat extraction was performed either in the presence or absence of a nitrogen overlay. Where applicable, nitrogen overlay was maintained by gassing the headspace of the container at 1 vvm using 100% nitrogen.

Figure 4:
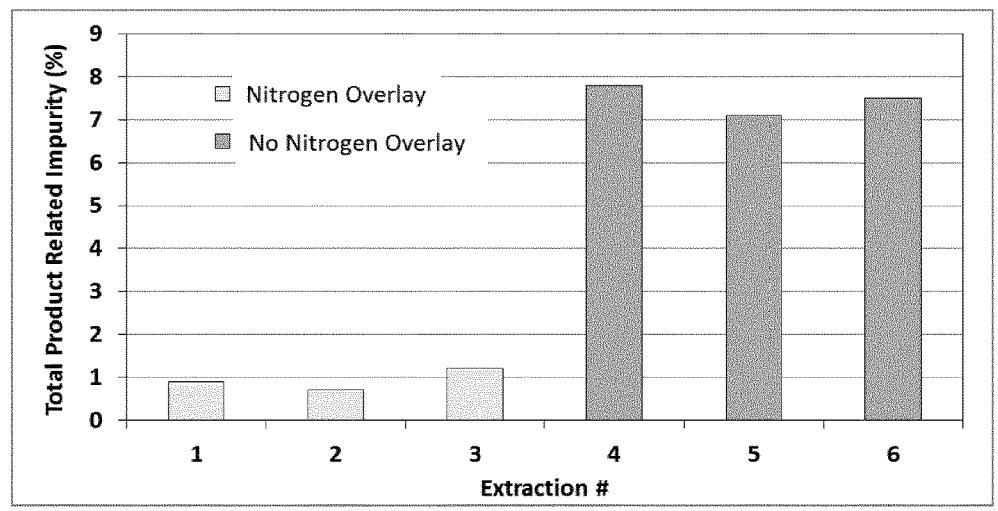
FIG. 4. Total Fab' fragments expressed as % of all product-related species as measured by CEX HPLC following Protein L purification. The results show again the benefit of the presence of nitrogen, resulting in significantly reduced levels of product related impurities remaining after heat extraction. A further beneficial effect is derived from the pH adjustment performed prior to heat extraction, as the levels of product-related impurities appear to be further reduced in comparison to previous examples.

In FIG. 4, extractions 1 to 3 were performed in the presence of a nitrogen overlay whereas extractions 4 to 6 were overlaid with air. The results show again the benefit of the presence of nitrogen, resulting in significantly reduced levels of product related impurities remaining after heat extraction. A further beneficial effect is derived from the pH adjustment performed prior to heat extraction, as the levels of product-related impurities appear to be further reduced in comparison to previous examples.

Example 4

The effect of extracting under reducing conditions was also analysed at a smaller scale, i.e. using shake flasks.

25-100 mL of protein-induced cell culture were harvested and resuspended in 250 mL Erlenmeyer flasks by the addition of water and 3× extraction buffer (pH 7.4) to a final 1× extraction buffer concentration (10 mM EDTA, 100 mM Tris). The flasks had a plug seal and were made of polycarbonate to minimize permeability of oxygen into the flask. The nitrogen overlay was added to the gaseous phase of the flasks using a disposable glove-bag (Aldrich AtmosBag, cat #Z530220) with a continuous flow of nitrogen through the glove-bag. Flasks were sealed before being removed from the glove bag and carrying out the heat extraction. Samples were also prepared on the bench (with air as an overlay in the gaseous phase of the flasks) for comparison. Heat extraction was carried out at 60° C. for 10 h in a shake flask incubator (New Brunswick Innova42). Redox potential was measured in each flask post-extraction using Broadley James ORP probes. The heat treatment step was also carried out at different flask fill volumes to assess the effect of different surface area to volume ratios on protein extraction. Table 3 summarises the experimental conditions tested.

TABLE 3

| Extraction # | Preparation | Fill Volume (mL) |
|---|---|---|
| 1 | Nitrogen | 25 |
| 2 | Nitrogen | 50 |
| 3 | Nitrogen | 100 |
| 4 | Air | 25 |
| 5 | Air | 50 |
| 6 | Air | 100 |

Figure 5:
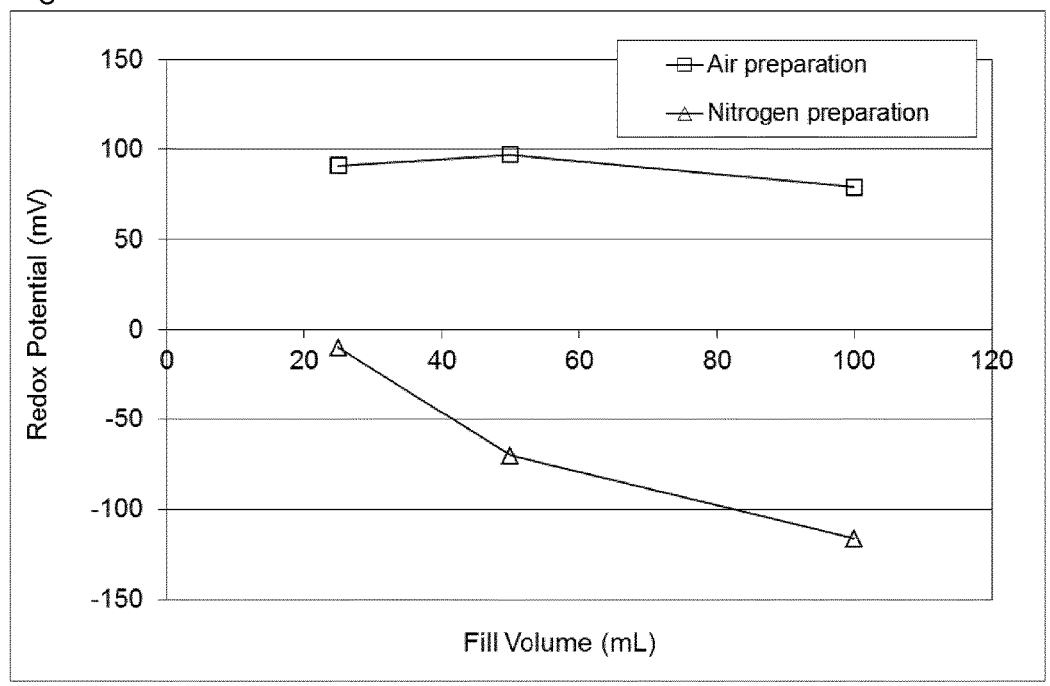
FIG. 5. Endpoint Redox potential measurement versus shake flask fill volume. These results demonstrate that the shake flasks which were prepared in the presence of a nitrogen overlay maintained a more reducing environment in the extract than the flasks which were prepared in the presence of air. The figure also shows that the flasks with a larger fill volume were more reducing than those with a smaller fill volume, likely due to a slower rate of oxidation of the extract due to the smaller surface area to volume ratio. The flasks prepared in air all had a positive endpoint redox potential value, with no correlation to fill volume.

FIG. 5 demonstrates that the shake flasks which were prepared in the presence of a nitrogen overlay maintained a more reducing environment in the extract than the flasks which were prepared in the presence of air. The figure also shows that the flasks with a larger fill volume were more reducing than those with a smaller fill volume, likely due to a slower rate of oxidation of the extract due to the smaller surface area to volume ratio. The flasks prepared in air all had a positive endpoint redox potential value, with no correlation to fill volume.

Figure 6:
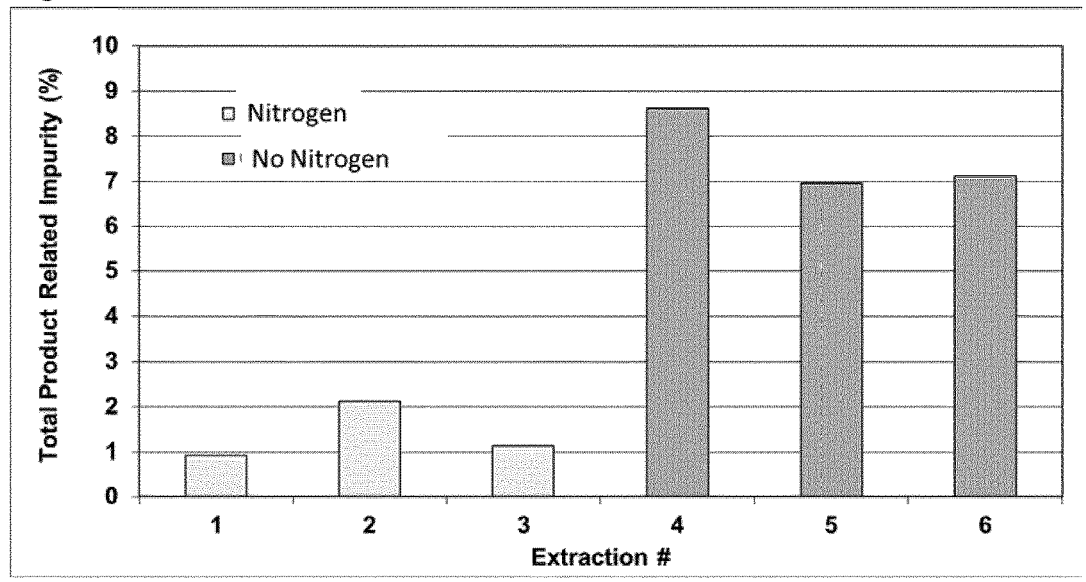
FIG. 6. Total Fab' fragments expressed as % of all product related species as measured by CEX HPLC following Protein L purification. These results show that the shake flasks which were prepared under nitrogen had significantly lower levels of product-related impurities post extraction. All nitrogen prepared flasks (endpoint redox potential range −10 mV to −116 mV) demonstrate significantly lower product-related impurity levels than all flasks prepared in air (endpoint redox potential range +79 mV to +97 mV).

FIG. 6 shows that the shake flasks which were prepared under nitrogen had significantly lower levels of product-related impurities post extraction. All nitrogen prepared flasks (endpoint redox potential range −10 mV to −116 mV) demonstrate significantly lower product-related impurity levels than all flasks prepared in air (endpoint redox potential range +79 mV to +97 mV).

Example 5

The Fab' binding specifically to human TNF-alpha has a higher melting temperature (Tm) than HCPs (host cell proteins), a feature that is exploited during the heat treatment step. The heating denatures a significant amount of HCPs and product-related impurities causing them to aggregate and be cleared during the extraction steps. However, as described in the preceding examples clearance of these impurities is greatly improved when a nitrogen overlay is applied, given the reduced redox potential. The reducing environment is believed to facilitate the clearance of the impurities due to reduction of the intra-chain bond in these species during heating, which would result in a decrease of the melting temperature in the impurities.

In order to confirm the above, the melting temperature of the two main species of product-related impurities was measured under non-reducing and reducing conditions. These reducing conditions were achieved by using TCEP-HCL (Tris (2-carboxyethyl) phosphine hydrochloride), to mimic the environment created by the nitrogen overlay carried out during the extraction.

Measurements were performed using a Thermofluor assay, based on the use of a hydrophobic fluorophore that binds to the protein provided some or all of its hydrophobic areas are exposed. In this particular case, the fluorophore was SYPRO orange (5000× concentration in DMSO; Life Technologies S-6650). This allows the unfolding process to be monitored under denaturing conditions (e.g. increasing temperatures) by measuring the fluorescence emitted by the dye when it is bound to the protein, using a real-time PCR system (7900HT fast real-time PCR system, from Life Technologies). Samples are incubated at increasing temperatures (from 25° C. to 99° C. with a 30 second hold and an increment of 0.5° C.) and the fluorescence emission recorded. The data is plotted and the melting point of the protein determined by finding the inflection point of the slope.

In this case the two purified product-related impurities were measured in citrate-phosphate buffer pH 5.0 and 7.0 and phosphate buffer saline pH 7.4. Two different concentrations of TCEP-HCL were used to achieve a reducing agent:protein molar ratio of 2:1 and 10:1, and a sample with no TCEP-HCL was run alongside as a control.

Figure 7:
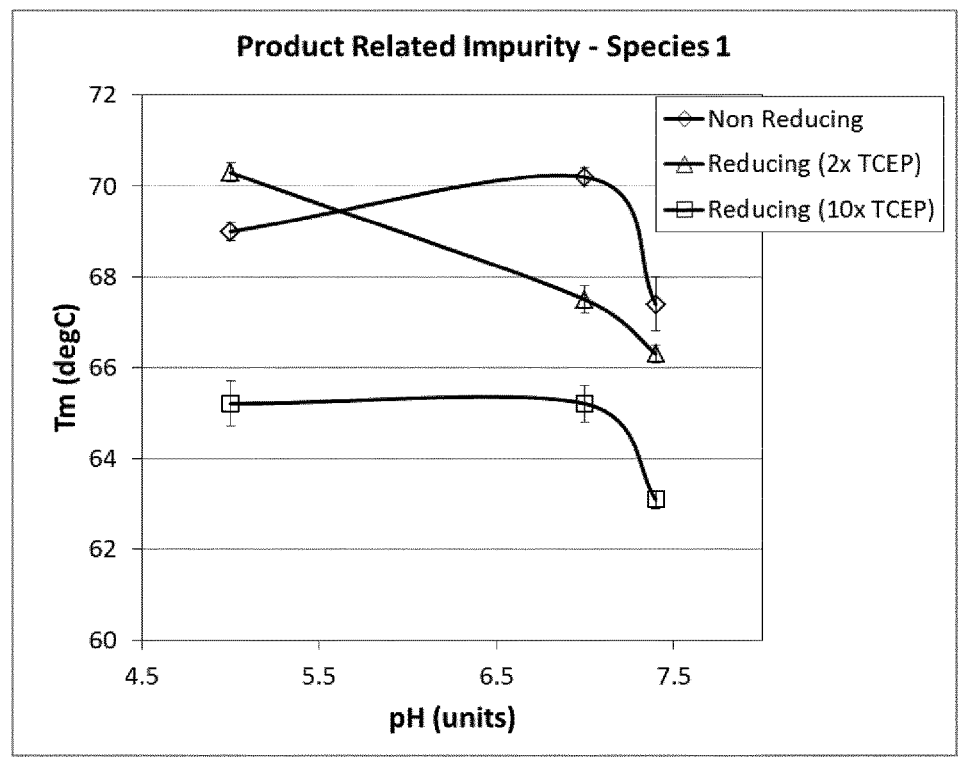
FIG. 7. Effect of pH and reducing environment on the Tm of purified Fab' fragments. The figure shows the results for the determination of the thermal stability for the two main species of product-related impurities. Redox potential and thermal stability (melting temperature) are shown to correlate; the lower the redox potential the lower the protein's melting temperature. A similar effect can be described for the pH when it becomes more neutral. Both variables would make the product-related impurities more prone to degradation, therefore facilitating their clearance.
Figure 7:
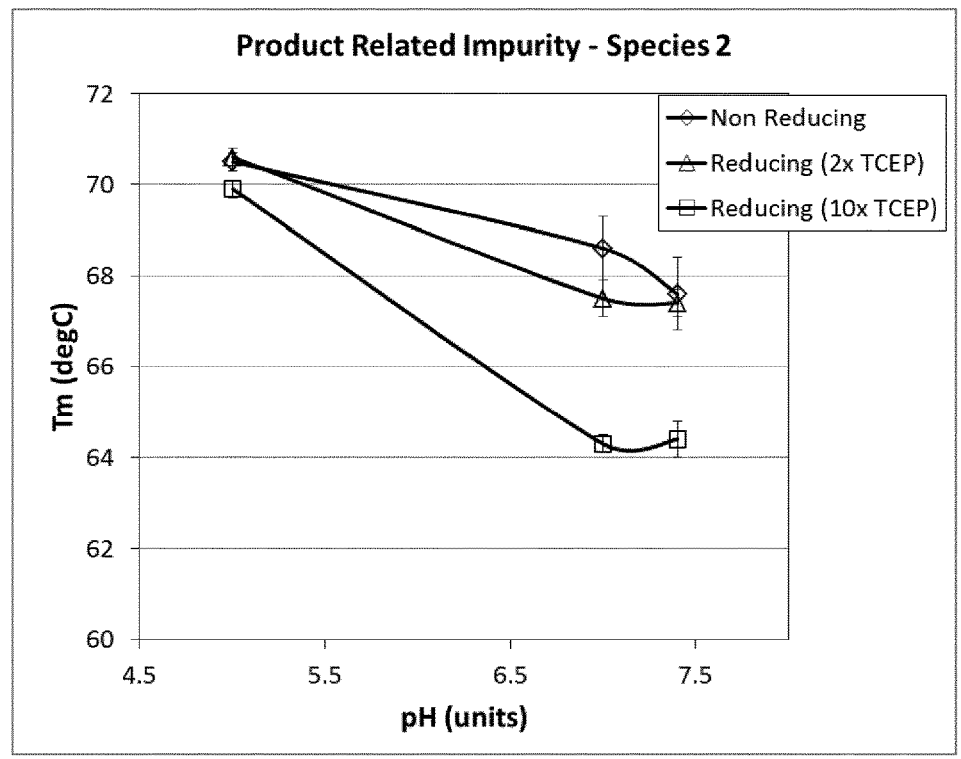

FIG. 7 shows the results for the determination of the thermal stability for the two main species of product-related impurities. Redox potential and thermal stability (melting temperature) are shown to correlate; the lower the redox potential the lower the protein's melting temperature. A similar effect can be described for the pH when it becomes more neutral. Both variables would make the product-related impurities more prone to degradation, therefore facilitating their clearance.

CONCLUSIONS

Overall, the data demonstrate the importance of maintaining a reducing environment (low redox potential) during the heating step to enable a significant reduction in levels of product-related impurities during protein extraction. Furthermore the data demonstrate that this reducing environment is enabled through the application of a nitrogen overlay and that when there is no nitrogen overlay, the redox potential of the environment is significantly less reducing which results in higher levels of product-related impurities.

The invention claimed is:

1. A method for manufacturing a protein of interest in a prokaryotic host cell comprising:
   a) culturing prokaryotic host cells under conditions such that said cells express a protein of interest having a higher melting temperature than the melting temperature of host cell proteins,
   b) collecting said host cells from the cell culture fluid,
   c) adding buffer to said host cells, and
   d) subjecting said host cells to heat treatment at a temperature of between 30° C. to 70° C. to melt host cell proteins while said protein of interest is not melted at said temperature and maintaining the redox potential of said buffer below −0 mV during said heat treatment.

2. The method according to claim 1, wherein the heat treatment is performed in a container and said redox potential is maintained by reducing the amount of oxygen ($O_2$) present in the gaseous phase in the container during protein extraction.

3. The method according to claim 2, wherein nitrogen ($N_2$) is added to the gaseous phase of the container.

4. The method according to claim 3, wherein said gaseous phase contains at least 50% $N_2$.

5. The method according to claim 3, wherein said $N_2$ is added to the container as an overlay in the gaseous phase of the container or by sparging the $N_2$ through the sample.

6. The method according to claim 1, wherein said heat treatment step is performed at 55° C. to 65° C.

7. The method according to claim 1, wherein said heat treatment is performed for a period of 1 to 18 hours.

8. The method according to claim 1, wherein the pH of the buffer, following addition to the host cells and prior to the heat treatment, is measured.

9. The method according to claim 8, wherein the pH of the buffer is a pH of 6 to 9 or is adjusted to a pH of 6 to 9.

10. The method according to claim 1, wherein the protein of interest is a recombinant protein encoded in an expression vector.

11. The method according to claim 10, wherein the protein of interest is a recombinant antibody.

12. The method according to claim 11, wherein said recombinant antibody is a recombinant antibody fragment that binds to an antigen.

13. The method according to claim 11, wherein said recombinant antibody specifically binds to TNF-alpha or CD154.

14. The method according to claim 12, wherein said antibody fragment specifically binds to TNF-alpha or CD154.

15. The method according to claim 12, wherein said recombinant antibody fragment is a Fab, Fab', F(ab')$_2$, Fv, scFv diabody, triabody, tetrabody, minibody, domain antibody (dAbs), sdAb, $V_HH$, $V_{NAR}$, single-chain antibody, a multispecific antibody formed from antibody fragments, Fab-Fv or Fab-Fv-Fv.

* * * * *